United States Patent [19]

Campagne

[11] 4,154,654

[45] May 15, 1979

[54] METHOD FOR PREPARING POLYSACCHARIDES

[75] Inventor: Jean-Claude Campagne, Saint-Vincent-la-Chatre, France

[73] Assignee: Rhone-Poulenc Industries, Paris, France

[21] Appl. No.: 771,361

[22] Filed: Feb. 23, 1977

[30] Foreign Application Priority Data

Feb. 26, 1976 [FR] France .................................. 76 05933

[51] Int. Cl.$^2$ ............................................ C12D 13/04
[52] U.S. Cl. ...................................... 195/31 P; 195/96
[58] Field of Search .................... 536/1; 195/31 P, 96, 195/100

[56] References Cited

U.S. PATENT DOCUMENTS

| | | | |
|---|---|---|---|
| 3,256,271 | 6/1966 | Schweiger | 195/31 P |
| 3,391,060 | 7/1968 | McNeely | 195/31 P |
| 3,406,114 | 10/1968 | Goven | 195/31 P |

*Primary Examiner*—Thomas G. Wiseman
*Attorney, Agent, or Firm*—Bacon & Thomas

[57] ABSTRACT

Polysaccharides, adapted for producing gels exhibiting high viscosity and improved filterability, are prepared by the controlled fermentation conversion of glucides with microorganisms of the Xanthomonas genus in the presence of an inorganic compound which is the sole source of assimilable nitrogen.

10 Claims, No Drawings

METHOD FOR PREPARING POLYSACCHARIDES

BACKGROUND OF THE INVENTION

1. Field of the Invention

The present invention relates, generally, to an improved process for the production of polysaccharides by fermentation of glucides in the presence of selected microorganisms and effective nitrogen-containing compounds; and, more especially to the fermentation of, e.g., sugars with a microorganism of the genus Xanthomonas in the presence of an inorganic nitrogen-containing compound which serves as the sole nitrogen source for the fermentation process.

2. Description of the Prior Art

Polysaccharide gels are known agents particularly adapted for, e.g., the assisted recovery of petroleum. Numerous and diverse processes are conventional for their preparation and include, inter alia, fermentation in the presence of certain microorganisms.

Conventionally, in the production of extracellular polysacchardies by fermentation of glucides with microorganisms, the medium to be fermented comprises a source of phosphorous, a source of magnesium which acts as an enzyme activator and a source of nitrogen. In the typical prior art processes to this end, the nitrogen is present as an organic compound which may consist of "distillers' solubles" (U.S. Pat. No. 3,000,790), of bran, whole cereal flours such as sorghum, soya, or maize (U.S. Pat. No. 3,271,267), or of "corn steep" (U.S. Pat. No. 3,355,447). However, these organic compounds, which provide the necessary assimilable nitrogen, suffer a significant disadvantage insofar as the same additionally introduce insoluble impurities which are, in turn, evident in the polysaccharide extracted from the fermented must.

Such unwanted impurities, in addition to imparting undesirable coloration and turbidity to the gel reconstituted from the extracted product, render that gel product unsuitable for certain uses such as, for example, the aforenoted assisted recovery of petroleum. Indeed, the presence of these impurities, which are of low solubility and consist of large protein molecules, reduces the filterability of the gels thereby obtained from the polysaccharides and, concomitantly, render it exceedingly more difficult for these gels to penetrate within the interstices of the rock formations. Consequently, in order to render these gels efficacious, it has become necessary to employ various subsequent techniques of purification, all of which are expensive and few of which are totally satisfactory in terms of yielding a usable product.

In an effort to overcome the problems attendant use of organic sources of nitrogen, various alternative techniques have been proposed. Most significant among these is the use of certain inorganic nitrogen compounds as a source of nitrogen for the production of polysaccharides by bacteriological conversion, especially by the Xanthomonas.

One such technique proposes the use of ammonium chloride as a source of nitrogen in these environments. See, M. P. Starr, "The nutrition of phytopathogenic bacteria-I. Minimal nutritive requirements of the genus Xanthomonas", *J. Bacteriology*, v. 51, pp. 131-143, 1946. However, while such compounds may be efficacious in the abstract, pragmatically they give rise to other problems more serious than that sought to be overcome, inasmuch as the presence of chloride ions in industrial apparatus causes severe corrosion of the equipment. This is significant not only in terms of the need to replace capital equipment, but by introducing the products of corrosion into the mixture.

Another alternative is proposed in the U.S. Pat. No. 3,391,060 to McNeely, which suggests the use of ammonium nitrate as a suitable source of nitrogen, its presence restricted to the final fermentation stage. Consequently, the process of McNeely requires the use of up to four prior process steps, which are conducted upon media principally containing soya peptone as the source of nitrogen. Also, in practicing the process of that patent, the concentration of ammonium nitrate in the final fermentation medium is critical to successful realization of the objects and advantages of the disclosed invention.

Therefore, the need exists to simply, economically, and yet efficiently provide a process for the production of polysaccharide gels, which gels exhibit the required high viscosity and yet, additionally, possess a high degree of filterability.

SUMMARY OF THE INVENTION

In accordance with the noted, and notable, deficiencies of the prior art, it is a primary object of the present invention to provide a simple, efficient, and economical process for the production of polysaccharide gels which exhibit high viscosity and good filterability.

It is also an object of the present invention to produce such polysaccharides by the fermentation conversion of glucides with a microorganism of the Xanthomonas genus.

Yet a further object of the present invention is to provide a process for the fermentation conversion of glucides with a microorganism of the genus Xanthomonas wherein the sole source of assimilable nitrogen is provided by an inorganic nitrogen-containing compound.

Yet further objects and advantages of the present invention will become apparent to the skilled artisan upon examination of the detailed description of the invention.

Surprisingly, it has been determined that the foregoing objects of the present invention may be realized by preparing an inoculum from a medium comprised of a microorganism of the Xanthomonas genus; subsequently inoculating a mixture comprising a glucide and an inorganic nitrogen-containing compound as the sole source of assimilable nitrogen in all process stages following preparation of the inoculum; and, fermenting the inoculated mixture to convert the glucide to a polysaccharide. The most preferred microorganism is *Xanthomonas campestris;* while the preferred inorganic nitrogen-containing compound is ammonium phosphate, most preferably diammonium phosphate. The glucide may be selected from any of a number of effective compounds, the sugars most preferred for the process of the present invention.

The fermentation mixture is maintained within a pH range of from about 6 to about 7.5, preferably from about 6.5 to 7.2, by a buffer agent such as dipotassium phosphate. Alternatively, if the medium is not buffered, a pH regulator may be employed to introduce requisite amounts of an alkaline reagent, such as sodium hydroxide, potassium hydroxide, or lime, which may or may not be in solution, into the medium.

Upon conversion of the glucide to the polysaccharide, the latter may be appropriately extracted as by, for example, precipitation, washed, dried and ground to a usable form for storage. Subsequently, by adding the ground polysaccharide to an aqueous solution, gels of the appropriate consistency may be produced, which gels exhibit both a high viscosity and good filterability.

DETAILED DESCRIPTION OF THE INVENTION

The present invention has, as its essence, the simple, economic and yet highly efficient, fermentation conversion of glucide to polysaccharide by the action of specific microorganisms, in the presence of an inorganic nitrogen-containing compound as the sole source of assimilable nitrogen at all process stages subsequent to the preparation of the inoculum. The polysaccharide, thus produced, exhibits both a desirably high viscosity and filterability, the latter characteristic of manifest importance in applications such as, for example, the assisted recovery of petroleum.

In order to more fully elucidate upon the various objects and advantages of the present invention, the following detailed description will be given in terms of certain preferred embodiments, and exemplified with respect thereto. However, the skilled artisan will appreciate that the same are illustrative, and in no wise limitative.

In the fermentation process of the present invention, it has been determined that it is possible to obtain, with the aid of microorganisms of the genus Xanthomonas, especially *Xanthomonas campestris*, a polysaccharide having improved properties by conducting the process in a restricted number of stages, not exceeding three. In all of the stages, save for the initial preparation of the inoculum, the process is conducted on media which contain, as the sole source of nitrogen, an inorganic nitrogen-containing compound. This inorganic compound is ammonium phosphate which, thus, also constitutes the requisite source of phosphorus needed for the fermentation process.

Since, as is conventional, it is necessary to conduct the fermentation at a pH within the range of from about 6 to about 7.5, and preferably within the range of from about 6.5 to 7.2, a buffer agent such as dipotassium phosphate is desirably added to the fermentation medium. However, this is not essential as it is equally feasible to employ a pH regulator for the introduction of requisite amounts of alkaline reagents such as, for example, sodium hydroxide, potassium hydroxide or lime, which may or may not be in solution.

Among the glucides which can be converted to polysaccharides by the instant process, there are included, inter alia, sucrose, glucose, fructose, wheat or corn starch, and their hydrolysis products, and the like. However, any functionally equivalent carbohydrate may be employed to this end.

The amount of ammonium phosphate employed as the sole source of nitrogen, following the preparation of the inoculum may vary widely. Thus, the ammonium phosphate may be present within a range of from about 1 to about 6 grams per liter, expressed as diammonium phosphate; but, preferably, the ammonium phosphate will be present within the range of from about 1.3 to about 3 grams per liter.

Typically, the inoculum is prepared by first inoculating a suitable broth with a culture of *Xanthomonas campestris* grown on an agar medium. The inoculation may be made by any conventional means including, for example, the use of a platinum loop.

Following preparation of the inoculum, that substance is employed to inoculate a sterile medium comprising the glucide and diammonium phosphate, along with adjuvants for buffering and the reduction of foaming. Following fermentation, under aerobic conditions, whereupon the glucide is converted to a polysaccharide, the latter may be isolated from the must in any conventional manner such as, for example, precipitation. To this end, a lower alcohol or acetone, or a mixture thereof, may be added to the must, after which the precipitate is isolated, washed, dried and ground. The product may then be employed to prepare gels having the high viscosity, and good filterability, of the present invention by addition to water or suitable aqueous solutions.

In order to further demonstrate the ease with which the improved polysaccharides of the present invention may be produced, the following examples will be given as illustrative, and not limitative.

EXAMPLE 1

A 500 cc Erlenmeyer flask is charged with 75 cc YM broth which is subsequently inoculated, by means of a platinum loop, with a culture of *Xanthomonas campestris* maintained on agar in a tube. The broth culture medium, obtained from DIFCO Chemical Company in dehydrated form, has the following composition:

| Component | Amount |
|---|---|
| Yeast extract for bacteriology | 3 g |
| Malt extract | 3 g |
| Soya peptone for bacteriology | 5 g |
| Pure glucose | 10 g |

This mixture is allowed to incubate at from about 28 to about 30° C. for about 48 hours and the resultant contents are employed to inoculate a sterile medium (6 liters), contained in a 10 liter laboratory fermenter and having a composition of:

| Component | Amount |
|---|---|
| Glucose | 20 g/l |
| Diammonium phosphate | 1.5 g/l |
| Dipotassium phosphate | 3 g/l |
| Magnesium sulphate heptahydrate | 0.25 g/l |
| Anti-foaming agent | 2 cc/l |
| Water (q.s.p.) | 6,000 cc ; | the dipotassium phosphate serving to buffer the pH of the composition within the range of from about 6.9 to about 7.5.

The composition is allowed to ferment, under stirring and aeration, for 64 hours at a temperature within the range of from about 28 to about 30° C. After that period, no glucose is found in the medium. The viscosity is measured on a Brookfield LVT viscometer at 30 rpm with a No. 4 needle and found to be 4,800 centipoise. The polysaccharide content is found to be 14.4 g/kg, corresponding to a yield of 72%.

EXAMPLE 2

The procedure of Example 1 is repeated to form the inoculant, which is introduced to a sterile medium (6 liters) having a composition of:

| Component | Amount |
|---|---|
| Sucrose | 20 g/l |

| Component | Amount |
|---|---|
| Diammonium phosphate | 1.3 g/l |
| Magnesium sulphate heptahydrate | 0.25 g/l |
| Anti-foaming agent | 2 cc/l |
| Water (q.s.p.) | 6,000 cc ; | the pH of the composition maintained at 6.7 by potassium hydroxide (KOH).

After 68 hours fermentation, with stirring and aeration, at a temperature within the range of from about 28° to about 30° C., all the sucrose is converted. The viscosity of the medium is 5,100 centipoise and the polysaccharide content is 15.3 g/kg, corresponding to a yield of 76.5%.

EXAMPLE 3

The procedure of Example 1 is repeated to form the inoculant, which is introduced to a sterile medium (6 liters) having a composition of:

| Component | Amount |
|---|---|
| Corn starch | 20 g/l |
| Diammonium phosphate | 3 g/l |
| Magnesium sulphate heptahydrate | 0.25 g/l |
| Anti-foaming agent | 2 cc/l |
| Water (q.s.p.) | 6,000 cc ; | the pH maintained at 6.8 during fermentation by sodium hydroxide (NaOH).

After 65 hours fermentation, the viscosity of the medium is 5,200 centipoise and the polysaccharide content is 15.1 g/kg, corresponding to a yield of 75.5%.

EXAMPLE 4

A 1 liter flask is charged with 150 cc of YM broth, which is inoculated by means of a platinum loop with a culture of Xanthomonas campestris maintained on agar in a tube. Following 48 hours incubation at a temperature within the range of from 28 to about 30° C., the contents of the flask are employed to inoculate a sterile medium (15 liters) contained in a 20 liter laboratory fermenter having a composition of:

| Component | Amount |
|---|---|
| Glucose | 10 g/l |
| Diammonium phosphate | 1.5 g/l |
| Dipotassium phosphate | 2 g/l |
| Magnesium sulphate heptahydrate | 0.25 g/l |
| Anti-foaming agent | 2 cc/l |
| Water (q.s.p.) | 15,000 cc ; | the pH maintained at from about 6.9 to about 7.5 by the buffering action of the dipotassium phosphate.

Following 40 hours incubation at a temperature within the range of from about 28° to about 30° C., under stirring and aeration, the contents of the fermenter are transferred, under sterile conditions, to a 13,000 liter fermenter containing a sterile medium (1,000 liters) having a composition of:

| Component | Amount |
|---|---|
| Glucose | 20 g/l |
| Diammonium phosphate | 1.5 g/l |
| Dipotassium phosphate | 5 g/l |
| Magnesium sulphate heptahydrate | 0.25 g/l |
| Anti-foaming agent | 2.5 cc/l |
| Water (q.s.p.) | 1,000 cc ; | the pH of the composition again maintained within the range of from about 6.9 to about 7.5 by dipotassium phosphate.

After 60 hours fermentation, under stirring and aeration, at a temperature within the range of from about 28° to about 30° C., no glucose is observed in the medium. The viscosity is 5,800 centipoise and the polysaccharide content is 14.8 g/kg, corresponding to a yield of 74%.

Isopropanol is added to a portion of this must, in conventional manner, to precipitate the polysaccharide, which is washed, dried, and ground. The powder thus obtained is employed in viscosity and filterability experiments in comparison with a conventional industrial polysaccharide obtained by fermentation on a medium containing a source of organic nitrogen.

Viscosity Experiments

The viscosity of gels prepared from the polysaccharide obtained in accordance with the present invention, and commercially available polysaccharides, is measured by means of a Brookfield LVT viscometer. The results thereof are summarized in Table I.

TABLE I

| Working conditions | Polysaccharide originating from the medium with inorganic nitrogen | Polysaccharide originating from the medium with organic nitrogen |
|---|---|---|
| 1% strength gel in water, needle No. 4 30 rpm | 2,700 cPs | 2,800 cPs |
| 0.3% strength gel in water, needle No. 2 3 rpm | 2,000 cPs | 2,000 cPs |
| 1% strength gel in water, UL adaptor, 0.6 rpm | 350 cPs | 340 cPs |

A review of the data of Table I indicates comparable viscosities for each polysaccharide, there being no significant differences between the two.

Filterability Experiments

A 0.1% strength gel in water is filtered through a Millipore filter of porosity 0.45 microns and diameter of 47 mm under an absolute pressure of 2.4 bars. Filterability is measured as the volume after 10 minutes.

The polysaccharide gel obtained by fermentation with a source of inorganic nitrogen in accordance with the present invention exhibits a filterability of 25 cc under the foregoing conditions. However, polysaccharide gels obtained by fermentation with a source of organic nitrogen in accordance with conventional prior art techniques exhibits a filterability of only 9 cc.

Accordingly, it is abundantly clear that the polysaccharide resulting from the method of the present invention yields gel products exhibiting viscosity characteristics at least as good as conventional polysaccharides obtained from a medium containing organic nitrogen, but exhibit a significantly higher filterability characteristic as compared therewith. Thus, the gels produced in accordance with the present invention are found to exhibit an enhanced utility for use in, for example, the assisted recovery of petroleum as the instant gels more readily penetrate into the interstices of rock formations encountered in such applications. Additionally, the need for further expensive, and not totally satisfactory, steps of purification are thereby eliminated.

While the present invention has now been described in terms of various preferred embodiments, and exemplified with respect thereto, the skilled artisan will readily appreciate that various modifications, changes, substitutions, and omissions may be made without departing from the spirit thereof. Accordingly, it is intended that the scope of the present invention be limited solely by that of the following claims.

What is claimed is:

1. Method of preparing a polysaccharide by fermentation of a glucide with a microorganism of the Xanthomonas genus, consisting essentially of the steps of:
    (a) preparing an inoculum from a medium comprising a microorganism of the genus Xanthomonas;
    (b) inoculating a medium comprising a glucide and a source of assimilable nitrogen consisting of ammonium phosphate with said inoculum;
    (c) fermenting the inoculated medium to convert said glucide to a polysaccharide; wherein the sole source of assimilable nitrogen in all stages following the preparation of the inoculum (a) is said ammonium phosphate; and,
    (d) isolating and recovering said polysaccharide.

2. The method of claim 1, wherein said microorganism in *Xanthomonas campestris.*

3. The method of claim 2, wherein said ammonium phosphate is diammonium phosphate.

4. The method of claim 3, wherein said diammonium phosphate is present in the range of from about 1 to about 6 grams per liter.

5. The method of claim 4, wherein said diammonium phosphate is present in the range of from about 1.3 to about 3 grams per liter.

6. The method of claim 3, wherein the pH during the fermenting step (c) is maintained within the range of from about 6 to about 7.5.

7. The method of claim 3, wherein the pH during the fermenting step (c) is maintained within the range of from about 6.5 to about 7.2.

8. The method of claim 3, further comprising the steps of:
    (e) washing the recovered polysaccharide;
    (f) drying said polysaccharide; and,
    (g) grinding said polysaccharide.

9. The method of preparing a polysaccharide gel comprising the step of adding the ground polysaccharide of claim 8 to an aqueous solution.

10. Method of preparing a polysaccharide by fermentation of a glucide with a microorganism of the Xanthomonas genus, consisting essentially of the steps of:
    (a) preparing an inoculum from a medium comprising a microorganism of the genus Xanthomonas;
    (b) inoculating a first medium comprising a glucide and a source of assimilable nitrogen consisting of ammonium phosphate with said inoculum to promote the growth of said microorganism;
    (c) inoculating a second medium comprising a glucide and a source of assimilable nitrogen consisting of ammonium phosphate with said inoculated first medium;
    (d) fermenting the inoculated second medium to convert said glucide to a polysaccharide; wherein the sole source of assimilable nitrogen in all stages following the preparation of the inoculum (a) is said ammonium phosphate; and,
    (e) isolating and recovering said polysaccharide.

* * * * *

Disclaimer 4,154,654.—*Jean-Claude Campagne*, Saint-Vincent-La-Chatre, France. METHOD FOR PREPARING POLY SACCHARIDES. Patent dated May 15, 1979. Disclaimer filed June 19, 1981, by the assignee, *Rhone-Poulenc Industries.*

Hereby enters this disclaimer to claims 1–10 of said patent.

[*Official Gazette November 17, 1981.*]